United States Patent
Gao et al.

(10) Patent No.: US 10,330,803 B2
(45) Date of Patent: Jun. 25, 2019

(54) POSITRON EMISSION TOMOGRAPHY IMAGING

(71) Applicant: Shenyang Neusoft Medical Systems Co., Ltd., Shenyang (CN)

(72) Inventors: Peng Gao, Shenyang (CN); Long Yang, Shenyang (CN); Guodong Liang, Shenyang (CN); Nan Li, Shenyang (CN); Yuqiu Zhao, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 41 days.

(21) Appl. No.: 15/281,092

(22) Filed: Sep. 30, 2016

(65) Prior Publication Data
US 2017/0153337 A1 Jun. 1, 2017

(30) Foreign Application Priority Data
Dec. 1, 2015 (CN) .......................... 2015 1 0866877

(51) Int. Cl.
*G01T 1/29* (2006.01)
*A61B 6/03* (2006.01)
(Continued)

(52) U.S. Cl.
CPC ............ *G01T 1/2985* (2013.01); *A61B 6/037* (2013.01); *A61B 6/0407* (2013.01); *A61B 6/0457* (2013.01); *G01T 1/175* (2013.01)

(58) Field of Classification Search
CPC .. G01T 1/64; G01T 1/24; G01T 1/164; A61B 6/037; A61B 6/0407; A61B 6/0457
See application file for complete search history.

(56) References Cited

U.S. PATENT DOCUMENTS 5,272,343 A * 12/1993 Stearns ................. G01T 1/2985
                                                              250/363.03
6,157,855 A * 12/2000 Sjoholm ............... A61B 5/0422
                                                              600/427
(Continued)

FOREIGN PATENT DOCUMENTS

CN 102631212 A 8/2012
CN 102648856 A 8/2012
(Continued)

OTHER PUBLICATIONS

"Star Network Topology", Wikipedia.org, accessed Sep. 7, 2018. (Year: 2018).*

Primary Examiner — Michael C Bryant
(74) Attorney, Agent, or Firm — Kilpatrick Townsend & Stockton LLP (57) ABSTRACT

A system and method of a PET imaging are provided. According to an example, a detector, a movement control module, a power control module and a reconstructing computer may be connected to a switch in a form of a star-shaped network topology. The detector may include M*N detector units distributed in an annular structure, each detector unit may be allocated with an IP address, M detector units are evenly distributed on each circumferential direction of the annular structure, and N detector units are evenly distributed on each axial direction of the annular structure. Each of the detector units may transmit a set of acquired data to the reconstructing computer through the switch via a network bus; and the set of data may include location information, acquiring time information and IP address. The reconstructing computer may perform a compliance process on all sets of data acquired by the detector according to the location (Continued)

information, acquiring time information and IP address, and reconstruct an image with the compliance data determined by the compliance process.

12 Claims, 4 Drawing Sheets

(51) Int. Cl.
*A61B 6/04* (2006.01)
*G01T 1/175* (2006.01)

(56) References Cited

U.S. PATENT DOCUMENTS

| | | |
|---|---|---|
| 7,139,367 B1 | 11/2006 | Le |
| 2004/0129886 A1 | 7/2004 | Lecoq |
| 2005/0067578 A1* | 3/2005 | Ueno ............... A61B 6/032 250/370.09 |
| 2007/0106154 A1 | 5/2007 | Conti |
| 2007/0152162 A1 | 7/2007 | Griesmer et al. |
| 2012/0166607 A1* | 6/2012 | Kitano ............... A61B 6/4233 709/223 |
| 2013/0114871 A1* | 5/2013 | Berkus ............... A61B 6/5205 382/131 |
| 2013/0240721 A1 | 9/2013 | Laurence |
| 2013/0343517 A1* | 12/2013 | Gagnon ............... G01T 1/24 378/19 |
| 2016/0267653 A1* | 9/2016 | Sasaya ............... G06T 11/003 |

FOREIGN PATENT DOCUMENTS

| | | |
|---|---|---|
| CN | 103070697 A | 5/2013 |
| CN | 103099639 A | 5/2013 |
| CN | 103458791 A | 12/2013 |
| CN | 104217447 A | 12/2014 |
| CN | 104820452 A | 8/2015 |
| JP | 2005257335 A | 9/2005 |
| JP | 2014228443 A | 12/2014 |
| WO | 2013050897 A1 | 4/2013 |

\* cited by examiner

| M0 N0 | | | | | | ...... | | | | | | | Mn N0 |
|---|---|---|---|---|---|---|---|---|---|---|---|---|---|
| M0 N1 | | | | | | ...... | | | | | | | Mn N1 |
| M0 N2 | | | | | | ...... | | | | | | | Mn N2 |
| M0 N3 | | | | | | ...... | | | | | | | Mn N3 |

POSITRON EMISSION TOMOGRAPHY IMAGING

BACKGROUND

The present disclosure relates to a position emission tomography (PET) imaging system and method.

According to the PET technology, a positron nuclides tracer of an extremely small amount may be injected into a subject such as a patient. The positrons released by the tracer may move in the subject and then combine with the negative electrons existed within the subject to cause an annihilation radiation and generate a pair of γ photons with the same energy and towards opposite directions. Then, the pair of γ photons may be acquired by a PET detector. Because travelling routes of the pair of γ photons in the subject are different, the time for reaching detectors of them may have some differences. If a detector system acquires a pair of γ photons at a 180 degree angle in a predetermined time length, the event may be referred to as a pair of compliance events. A PET image may be reconstructed by processing and calculating the compliance events, so as to reflect the physiological function and structure of organs of the subject.

A PET system may include a plurality of components, such as a detector, a data acquiring circuit, a data processing circuit, a scanning bed, a communication interface, a control computer, and a reconstructing computer, etc. The communication bus between the plurality of components may include such as Controller Area Network (CAN) bus, 485 bus, and Ethernet, etc. Due to the facts that there are a plurality of buses and the communication protocols between these buses may be different from each other, a plurality of bus control modes may be used, thereby causing transmission of instructions and data to be relative complex. Furthermore, a compliance process performed on a set of data may be a hard compliance on-line process. For example, the data acquiring circuit may transmit the data acquired from the detector to the data processing circuit. The data processing circuit may perform a compliance process on the set of data through a hardware and transmit the set of data after the compliance process to the reconstructing computer. And thereby, the reconstructing computer may reconstruct an image with the set of data after the compliance process.

Some data may be discarded during a compliance process performed by the data processing circuit. Then, during the process of subsequent image calibration, the reconstructing computer may need to recover the discarded data so as to improve accuracy of the final image calibration.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS' s latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

BRIEF DESCRIPTION OF DRAWINGS

Features of the present disclosure are illustrated by way of example and not limited in the following figures, in which like numerals indicate like elements, in which.

DETAILED DESCRIPTION

Figure 1:
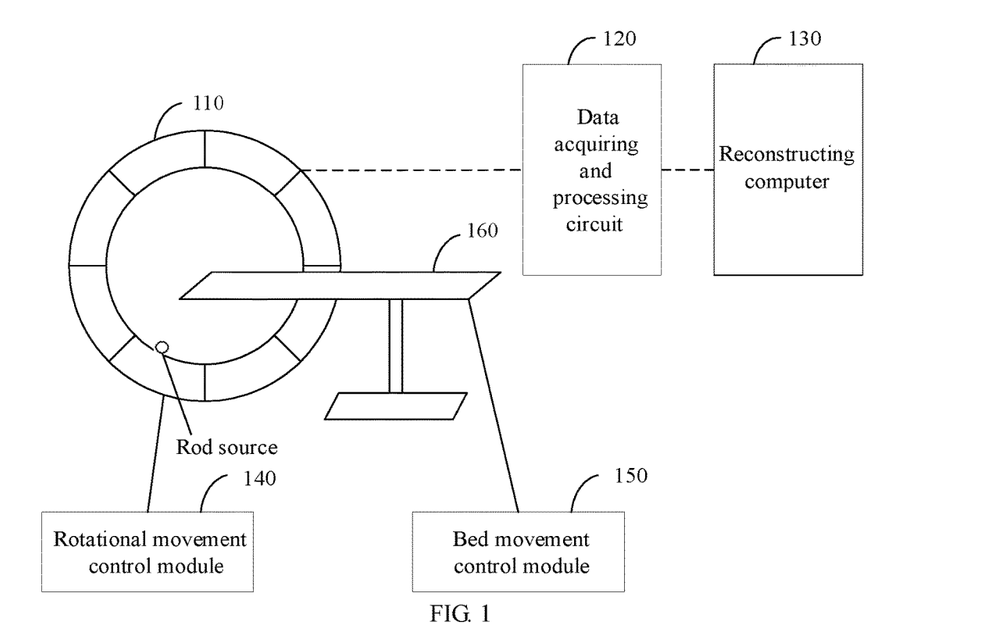
FIG. 1 is an architecture diagram of a PET imaging system.

The basic architecture of a PET system may be firstly introduced before introduction of a technical scheme of the present disclosure. FIG. 1 is an architecture diagram of a PET imaging system.

The scintillation crystal on the detector 110 may convert γ photons into fluorescence and the photomultiplier tube (PMT) may convert an optical signal to an electrical signal. The data acquiring and processing circuit 120 may transmit the acquired and processed electrical signals (it may also be referred to as "data" hereinafter) to the reconstructing computer 130 to reconstruct a scanning image based on the received data.

In the PET imaging system, the rotational movement control module 140 may be used to control movement of a rod source (not shown in the FIG. 1) and may use a kind of communication protocol to communicate with the detector 110. The bed movement control module 150 may be used to control movement of the scanning bed 160 and may use another kind of communication protocol to communicate with the scanning bed 160. In addition, still another kind of communication protocol may be used between the detector 110 and the reconstructing computer 130. This communication mode may be relatively complicated.

Figure 2A:
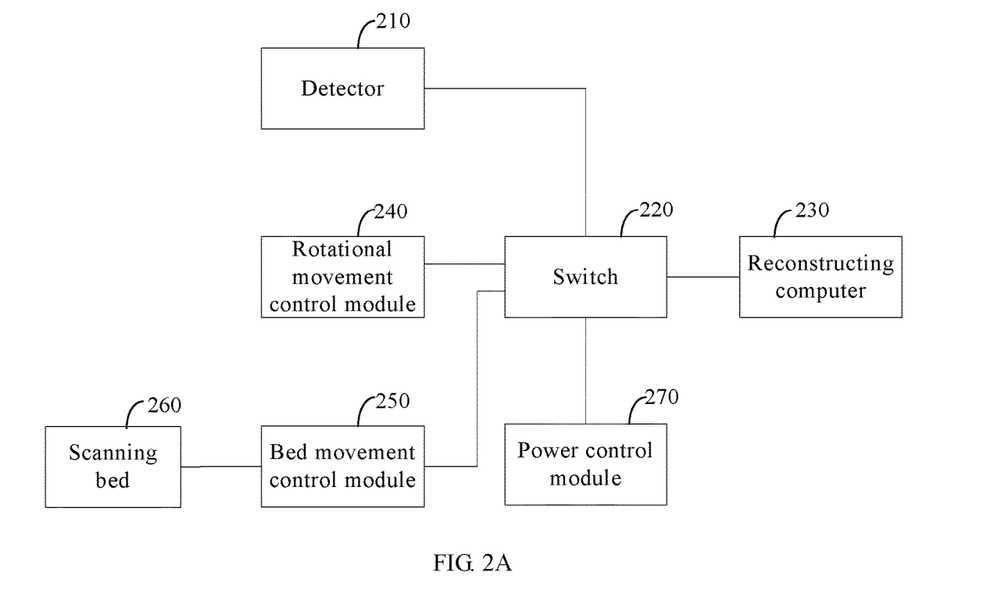
FIG. 2A is an architecture diagram of a PET imaging system according to an example of the present disclosure.

FIG. 2A is an architecture diagram of a PET imaging system according to an example of the present disclosure.

The PET imaging system may include the following components a detector 210, a switch 220, a reconstructing computer 230, a rotational movement control module 240, a bed movement control module 250 and a power control module 270. The rotational movement control module 240 may be used to control movement of a rod source in the PET imaging system. The bed movement control module 250 may be used to control the vertical and lateral movements of the scanning bed 260. In an example, each movement control module may be regarded as an independent module, i.e., each of the rotational movement control module 240 and the bed movement control module 250 may be allocated with an Internet Protocol (IP) address. The power control module 270 may be used to control power supply for various components in the overall system. The detector 210, the rotational movement control module 240, the bed movement control module 250, the power control module 270 and the reconstructing computer 230 may be connected to the switch 220 in a form of a star-shaped network topology.

In the overall system of the present disclosure, all the components may be connected to the switch 220 via a network bus, and communication between all the components may be realized based on the star-shaped network topology via a single kind of communication protocol. In this way, comparing with the communication realized by adopting different kinds of communication protocols between a plurality of buses, the communication realized by a single kind of communication protocol may decrease complexity of control and communication.

The detector 210 may have an annular structure. For example, the detector 210 may include M*N detector units, M detector units are evenly distributed on each circumferential direction of the annular structure, and N detector units are evenly distributed on each axial direction of the annular structure. Each of the detector units may be allocated with an IP address. Both M and N are integers greater than 1.

Figure 2B:
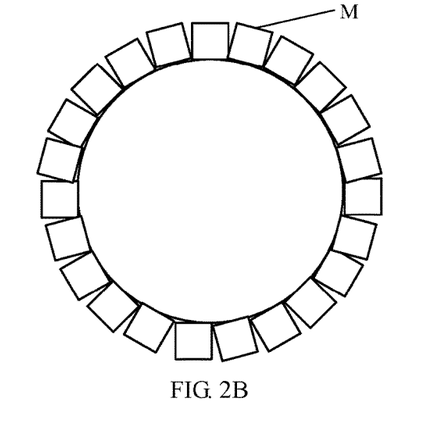
FIG. 2B is a cross-sectional view of a PET detector in the axial direction according to an example of the present disclosure.
Figure 2C:
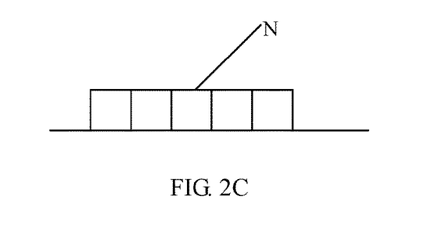
FIG. 2C is a cross-sectional view of a PET detector in the radial direction according to an example of the present disclosure.

The detailed structure of the detector 210 may refer to FIG. 2B and FIG. 2C. FIG. 2B is a cross-sectional view of the detector in the axial direction and FIG. 2C is a cross-sectional view of the detector in the radial direction. As can be seen in FIG. 2B, the detector may comprise M detector units in each circumference direction. As can be seen in FIG. 2C, the detector may comprise N detector units in each axial direction. In this case, the detector may comprise M*N detector units.

For example, M may be 100 and N may be 6. It should be noted that the number of M and N is not limited in the present disclosure and may be chosen according to actual requirements.

It should be noted that the number of M and N may be configured. For example, after the size of the circumference of the detector and the size of each detector unit are determined, the number of M may be determined. The number of N may be configurable as needed and not limited due to being on the axial direction.

As for the reconstructing computer 230, the increase and decrease of the number of M and N may be only to increase or decrease a node, i.e., increase or decrease an IP address. The number of the detector unit in the system may be easy to be changed, thereby having a wider practicability.

It should be appreciated that the reconstructing computer 230 may obtain IP addresses corresponding to various components and establish a mapping table to facilitate data interaction and control with various components.

Various detector units of the detector 210 may transmit the acquired data to the reconstructing computer 230 through the switch 220 via the network bus. The data transmitted by various detector units of the detector 210 may include location information, acquiring time information and IP address, etc.

It should be noted that each of the detector units of the detector 210 may transmit a set of data to the reconstructing computer 230 either in series or in parallel. It should be appreciated that each of the detector units may be a node and the set of data acquired by each node may be transmitted to the reconstructing computer 230.

It should be appreciated that the location information may refer to three-axis coordinate of a γ photon. Because the location information of the photon may be needed when an image is reconstructed, i.e., the location where a γ photon is acquired by the detector. The acquiring time information may refer to the time when a set of data is acquired by the detector. The IP address may indicate a detector unit transmitting the set of data.

Specifically, each of the detector units may comprise a crystal, a photoelectric conversion element and a sampling circuit. It should be appreciated that any known technology or structure may be used to realize the crystal, photoelectric conversion element and sampling circuit of each of the detector units. Where, the crystal may include but is not limited to Bismuth Germanium Oxide (BGO), Lutetium-yttrium oxyorthosillicate scillation crystal (LYSO); the function of the photoelectric conversion element may convert a acquired optical signal to an electrical signal and may include but is not limited to a photomultiplier tube (PMT) and a Silicon Photomultiplier (SiPM); and the sampling circuit may be mainly used to finish digitization of electrical signals.

The reconstructing computer 230 may be used to perform a compliance process on all sets of data acquired by the detector according to location information, acquiring time information and IP address, and reconstruct an image with the compliance data determined by the compliance process.

In the provided PET imaging system of the disclosure, the detector, the rotational movement control module, the bed movement control module, the power control module and the reconstructing computer may be connected to the switch in a form of a star-shaped network topology, thus communication protocols between the network bus are unified and data interaction is convenient due to a fact that a single network bus may be used to communicate between various components. Furthermore, each of the detector units may have independent data transmission function and may directly transmit the acquired data to the reconstructing computer without special data processing circuit. In addition, the reconstructing computer may obtain the original data acquired by each of the detector units, rather than the remaining data after the data processing circuit discards partial data, thus the efficiency of a compliance process performed by the reconstructing computer may be improved and recovering the discarded data may be not required.

Figure 3:
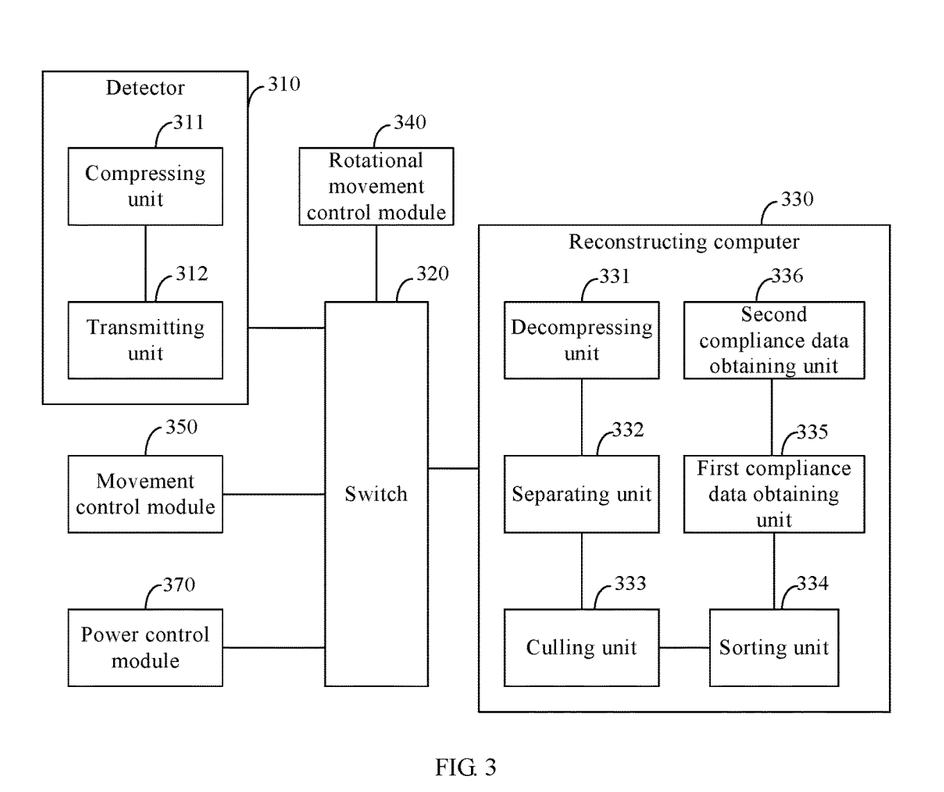
FIG. 3 is an architecture diagram of a PET imaging system according to another example of the present disclosure.

FIG. 3 is an architecture diagram of a PET imaging system according to another example of the present disclosure.

In the provided PET imaging system of the disclosure, each of the detector units 310 may comprise a compressing unit 311 and a transmission unit 312. The detector unit may transmit the acquired data to the reconstructing computer 330 through the switch 320 via the network bus.

The compressing unit 311 may be used to compress a set of data acquired by a detector unit in a preset period into a packet. It should be appreciated that the preset period may be set according to actual requirements, for example, the preset period may be 50 us or 100 us. Each of the detector units in a preset period may acquire the data within a plurality of acquiring periods, such as three acquiring periods. Thus in a preset period, the compressing unit 311 may compress a set of data acquired within three acquiring periods into a packet when the set of data is transmitted.

It should be noted that transmitting the packet to the reconstructing computer in the preset period may require each of the detector units to transmit a set of acquired data in the preset period to the reconstructing computer.

The transmission unit 312 may be used to sequentially transmit the packet to the reconstructing computer 330 through the switch via the network bus according to an arrangement of the annular structure.

It should be noted that M*N detector units may sequentially transmit the packet either in series, or in parallel in rows or columns according to the arrangement of the annular structure. For example, M*N packets within the first acquiring period may be firstly transmitted, then M*N packets within the second acquiring period may be transmitted, and so on.

In order to make those skilled in the art more intuitively understand the detailed form of transmitting a set of data by a detector unit, the description may be given in detail in combination with the following tables.

For convenience of description, M=8, N=4, M*N=32 detector units are introduced, where N is the row and M is the column. It should be appreciated that N may also be the column and M may be the row. The following examples are introduced with N as the row and M as the column.

Figure 2D:
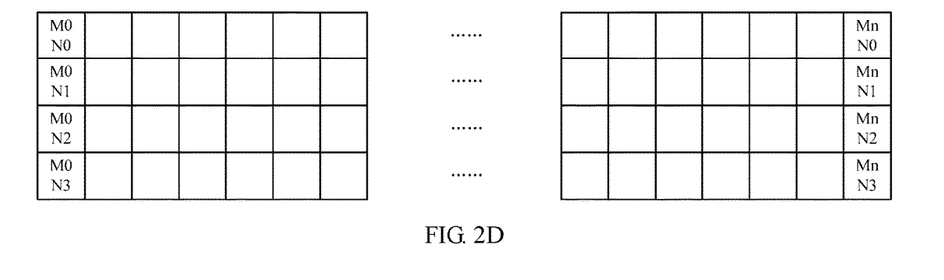
FIG. 2D is a schematic expanded view of a PET detector in a plane coordinate system according to an example of the present disclosure.

FIG. 2D illustrates a schematic expanded view of the detector 310 in a rectangular coordinate system and the arrangement of 32 detector units is shown in the table 1.

TABLE 1

| M0N0 | M1N0 | M2N0 | M3N0 | M4N0 | M5N0 | M6N0 | M7N0 |
|------|------|------|------|------|------|------|------|
| M0N1 | M1N1 | M2N1 | M3N1 | M4N1 | M5N1 | M6N1 | M7N1 |
| M0N2 | M1N2 | M2N2 | M3N2 | M4N2 | M5N2 | M6N2 | M7N2 |
| M0N3 | M1N3 | M2N3 | M3N3 | M4N3 | M5N3 | M6N3 | M7N3 |

It should be appreciated that the 32 detector units may transmit the packet to the reconstructing computer in series. For example, the sequence when transmitting in series may be as follows: M0N0, M1N0, M2N0, M3N0, M4N0, M5N0, M6N0, M7N0, M0N1, M1N1, M2N1, M3N1, M4N1, M5N1, M6N1, M7N1, M0N2, M1N2, M2N2, M3N2, M4N2, M5N2, M6N2, M7N2, M0N3, M1N3, M2N3, M3N3, M4N3, M5N3, M6N3, M7N3.

For example, the sequence when transmitting in parallel may be as follows, i.e., the 4-row data are simultaneously transmitted in parallel:

M0N0, M1N0, M2N0, M3N0, M4N0, M5N0, M6N0, M7N0;

M0N1, M1N1, M2N1, M3N1, M4N1, M5N1, M6N1, M7N1;

M0N2, M1N2, M2N2, M3N2, M4N2, M5N2, M6N2, M7N2;

M0N3, M1N3, M2N3, M3N3, M4N3, M5N3, M6N3, M7N3.

In an example, the preset period for transmitting the packet may comprise n acquiring periods and n is an integer greater than 1. The data acquired by the detector unit may include data index, indicating whether the data is valid or not.

The reconstructing computer 330 may comprise a decompressing unit 331, a separation unit 332 and a culling unit 333. The decompression unit 331 may be used to decompress the packet transmitted by the transmission unit 312 into a set of decompressed data. The separation unit 332 may be used to separate the set of decompressed data according to the acquiring period. For example, when n is 3, i.e., each preset period comprises three acquiring periods and each of the detector units acquires once data within each acquiring period.

The relationship between the preset period and acquiring period may be intuitively understood with reference to Table 2 and Table 3.

TABLE 2

| Total data | | | | |
|---|---|---|---|---|
| A packet within preset period 1 | A packet within preset period 2 | A packet within preset period 3 | A packet within preset period 4 | ... |
| Acquiring period 0, 1, 2 | Acquiring period 0, 1, 2 | Acquiring period 0, 1, 2 | Acquiring period 0, 1, 2 | ... |

TABLE 3

| the data corresponding to each acquiring period | | |
|---|---|---|
| Acquiring period 0 | Acquiring period 1 | Acquiring period 2 |
| M0N0 | M0N0 | M0N0 |
| M1N0 | M1N0 | M1N0 |

TABLE 3-continued

| the data corresponding to each acquiring period | | |
|---|---|---|
| Acquiring period 0 | Acquiring period 1 | Acquiring period 2 |
| M2N0 | M2N0 | M2N0 |
| ... | ... | ... |
| M0N7 | M0N7 | M0N7 |
| M1N7 | M1N7 | M1N7 |
| M7N7 | M7N7 | M7N7 |

Table 3 illustrates the arranged data in accordance with a acquiring period within each preset period.

The data structure of a single acquiring period may be shown in Table 4.

TABLE 4

| Acquiring period 0 | | | |
|---|---|---|---|
| M0N0 | M0N1 | M0N2 | M0N3 |
| M1N0 | M1N1 | M1N2 | M1N3 |
| M2N0 | M2N1 | M2N2 | M2N3 |
| M3N0 | M3N1 | M3N2 | M3N3 |
| M4N0 | M4N1 | M4N2 | M4N3 |
| M5N0 | M5N1 | M5N2 | M5N3 |
| M6N0 | M6N1 | M6N2 | M6N3 |
| M7N0 | M7N1 | M7N2 | M7N3 |

The culling unit 333 may be used to obtain a set of valid data by eliminating invalid data from the set of data separated by the separation unit according to the acquiring period and the corresponding data index.

It should be noted that the data index may indicate the time corresponding to the valid data. That is because the time a γ photon generates is random, the data may not be acquired at all of the acquiring periods and the data corresponding to a detector unit without acquiring any data may be eliminated via the data index.

The process of the elimination may refer to Table 5.

TABLE 5

| Acquiring period 0 | Acquiring period 1 | Acquiring period 2 |
|---|---|---|
| Valid data | Valid data | Invalid data |
| Valid data | Valid data | Invalid data |
| Valid data | Valid data | Invalid data |
| Valid data | Valid data | Invalid data |
| Invalid data | Valid data | Invalid data |
| Invalid data | Valid data | Invalid data |
| Invalid data | Valid data | Invalid data |

In Table 5, the areas filled with oblique lines may represent the valid data and the blank areas may represent the invalid data. For example, the acquiring period 2 does not include valid data, thus the data amount to be processed is 0 within the acquiring period 2. That is, the reconstructing computer 330 may only need to perform a compliance process on the set of valid data with the oblique lines.

Continuing with the example of Table 4, it is assumed that all the detector units acquire data within the acquiring period 0 as shown in Table 4. However, in practical, there are some detector units which may not acquire any data within the acquiring period 0, thus invalid data should be eliminated. The valid data after the elimination performed on the data within the acquiring period 0 as shown in Table 4 may be shown in Table 6.

TABLE 6

| Acquiring period 0 | | | |
|---|---|---|---|
| M0N0 | M0N1 | M0N2 | M0N3 |
| M1N0 | M1N1 | M1N2 | M1N3 |
|  | M2N1 |  |  |
|  |  | M3N2 | M3N3 |
| M4N0 | M4N1 | M4N2 |  |
| M5N0 | M5N1 | M5N2 |  |
|  |  |  | M6N3 |
| M7N0 | M7N1 | M7N2 | M7N3 |

The reconstructing computer 330 may further comprise: a sorting unit 334, a first compliance data obtaining unit 335 and a second compliance data obtaining unit 336.

Where the sorting unit 334 may be used to sort the set of valid data for each of the acquiring periods in a chronological order of the acquiring time information. It should be noted that the sorting in an order of the acquiring time may take the acquiring period as a unit, i.e., the data for each of the acquiring periods are sorted in a chronological order of the acquiring time. For example, the set of valid data shown in Table 6 after being sorted in the chronological order of the acquiring time may be as follows: M0N0, M1N0, M4N0, M5N0, M7N0, M0N1, M1N1, M2N1, M4N1, M5N1, M7N1, M0N2, M1N2, M3N2, M4N2, M5N2, M7N2, M0N3, M1N3, M3N3, M6N3, M7N3.

The first compliance data obtaining unit 335 may be used to obtain a set of first compliance data in a predetermined time length by cutting the sorted set of data with a time window of the predetermined time length. For example, the time window of the predetermined time length may be 6 ns, i.e., and the sorted set of data are cut with the 6 ns as a time unit.

For example, the sorted set of data may be cut according to a time window of the predetermined time length, so as to obtain the first compliance data, which are shown in Table 7.

TABLE 7

| time window 1 | time window 2 | time window 3 | time window 4 | time window 5 | time window 6 | time window 7 | time window 8 | time window 9 | time window 10 |
|---|---|---|---|---|---|---|---|---|---|
| M0N0 | M4N0 | M7N0 | M2N1 | M5N1 | M0N2 | M3N2 | M5N2 | M7N2 | M3N3 |
| M1N0 | M5N0 | M0N1 | M4N1 | M7N1 | M1N2 | M4N2 |  | M0N3 | M6N3 |
|  |  | M1N1 |  |  |  |  |  | M1N3 |  |

It can be seen from the Table 7 that the time window of the predetermined time length cuts two sets of data, the time window 3 cuts three sets of data and the time window 8 cuts a set of data. It should be noted that if the time window of the predetermined time length cuts only a set of data, the set of data may not participate in the subsequent compliance process. If the time window of the predetermined time length cuts two or more sets of data, the two or more sets of data may participate in the subsequent compliance process.

The above is a time compliance process performed on all sets of data transmitted by the detector 310 and a space compliance process performed on all sets of data transmitted by the detector 310 will be described hereinafter.

The second compliance data obtaining unit 336 may be used to obtain a set of second compliance data by selecting a pair of compliance data within a predetermined position area from the set of first compliance data according to the location information and IP address. The set of second compliance data may be used to reconstruct an image.

The predetermined position area may refer to a range of the PET field of view (FOV). For example, a range of a FOV may be 270 degrees and a pair of data in the range of 270 degrees may be the second compliance data.

In the system provided in the disclosure, the reconstructing computer 330 may receive all sets of original data transmitted by the detector 310, next all sets of data may be separated according to the acquiring period, and then invalid data (i.e. blank data) in the separated set of data may be eliminated according to the acquiring period and the corresponding data index. The set of valid data for each of the acquiring periods may be sorted in a chronological order of the acquiring time, then a set of first compliance data may be obtained by cutting the sorted set of data with a time window of the predetermined time length, finally a set of second compliance data may be obtained by selecting a pair of compliance data within a predetermined position area from the set of first compliance data, where, the set of second compliance data may be used to reconstruct an image. Thus it can be seen that the compliance process performed on the sorted set of data may be directly performed by the reconstructing computer without the data discarded by other circuits and then performed the compliance process by the reconstructing computer. Thus the reconstructing computer may efficiently obtain a pair of compliance data.

In addition, it should be noted that the data transmitted by the detector 310 to the reconstructing computer 330 may include energy information in addition to the location information, acquiring time information, data index and IP address. That is because the acquiring effect of different crystals may be inconsistent during the detector 310 for acquiring energy. It may be assumed that a detector unit includes 100 crystals, due to different physical positions corresponding to 100 crystals, and the response to light may be inconsistent. There may be a certain proportionate relationship between the response to light and energy. When the acquired energy is relatively low, a single photon event may not be generated, but the single photon event is the basis of a pair of compliance event. Therefore, before the reconstructing computer 330 performs a compliance process on the sorted set of data, it may also need to calibrate a photon by using the energy information.

The present disclosure further provides a method of a PET imaging based on the PET imaging system provided in the above and will be described in detail in combination of the figures.

Figure 4:
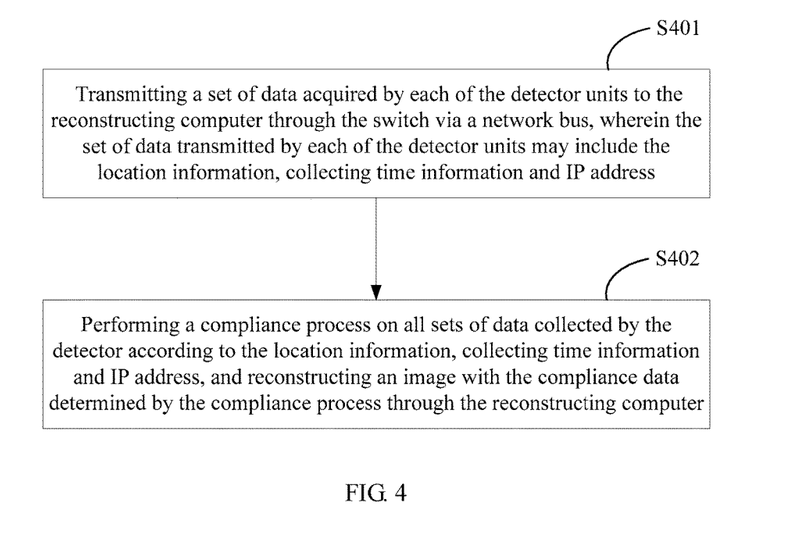
FIG. 4 is a flowchart illustrating a method of a PET imaging according to an example of the present disclosure.

FIG. 4 is a flowchart illustrating a method of a PET imaging according to an example of the present disclosure.

The method of a PET imaging provided by the disclosure may be applied to a PET imaging system. The system may comprise a detector, a rotational movement control module, a bed movement control module, a power control module, a switch and a reconstructing computer. The detector, the movement control module, the power control module and the reconstructing computer may be connected to the switch in a form of a star-shaped network topology.

The detector may have an annular structure. For example, the detector may include M*N detector units, M detector units may be evenly distributed on each circumferential direction of the annular structure, and N detector units may be evenly distributed on each axial direction of the annular structure. Each of the detector units may be allocated with an IP address. Both M and N are integers greater than 1. The rotational movement control module, the bed movement control module and the power control module may be allocated with an IP address respectively.

For example, M is 100 and N is 6. It should be noted that the number of M and N is not limited in the present disclosure and may be chosen according to actual requirements.

It should be noted that the number of M and N may be configured. For example, after the size of the circumference of a detector and the size of each detector unit are determined, the number of M may be determined. The number of N may be configurable as needed and not limited due to being on the axial direction.

As shown in FIG. 4, the method of a PET imaging may comprise the following steps.

In the step S401, each of the detector units may transmit a set of acquired data to the reconstructing computer through the switch via a network bus, where the set of data transmitted by each of the detector units may include the location information, acquiring time information and IP address.

It should be noted that each of the detector units may transmit a set of data to the reconstructing computer either in series or in parallel. It should be appreciated that each of the detector units is a node and the set of data acquired by each node may be transmitted to the reconstructing computer.

It should be appreciated that the location information may refer to three-axis coordinate of a γ photon. Because the location information of the photon may be needed when an image is reconstructed, i.e., the location where a γ photon is acquired by the detector. The acquiring time information may refer to the time when a set of data is acquired by the detector. The IP address may indicate a detector unit transmitting the set of data.

In the step S402, the reconstructing computer may perform a compliance process on all sets of data acquired by the detector according to the location information, acquiring time information and IP address and reconstruct an image with the compliance data determined by the compliance process.

In an example, the detector, the rotational movement control module, the bed movement control module, the power control module and the reconstructing computer may be connected to the switch in a form of a star-shaped network topology, thus the communication protocols between the network bus are unified and data interaction is convenient due to a fact that a single network bus may be used to communicate between various components. Furthermore, each of the detector units may have independent data transmission function, thus may directly transmit the acquired data to the reconstructing computer without special data processing circuit. Thus, the reconstructing computer may obtain all sets of original data acquired by the detector, rather than the remaining data after the data processing circuit discards partial data, thus the efficiency of a compliance process performed by the reconstructing computer may be improved and recovering the discarded data may be not required.

Figure 5:
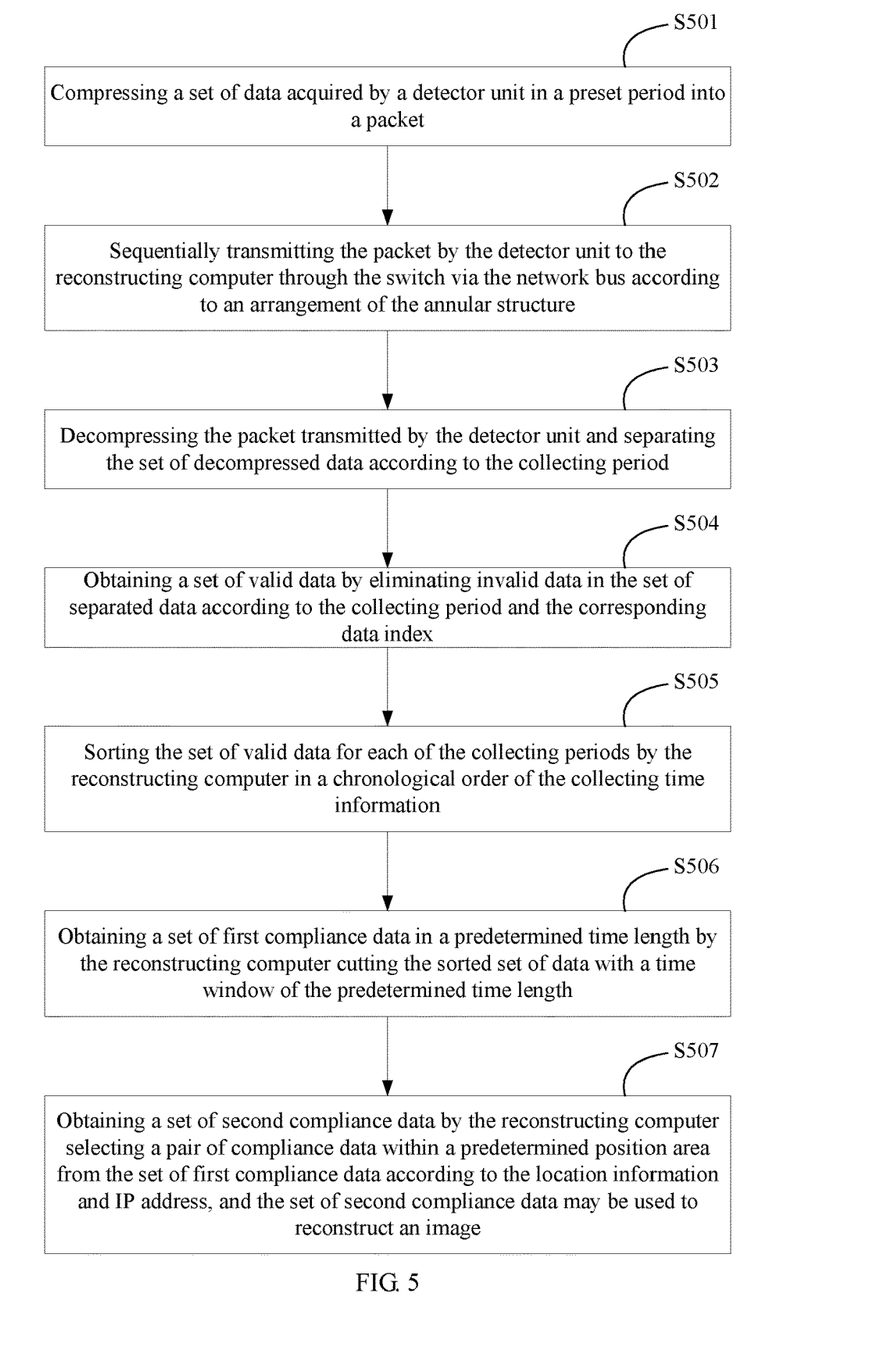
FIG. 5 is a flowchart illustrating a method of a PET imaging according to another example of the present disclosure.

FIG. 5 is a flowchart illustrating a method of a PET imaging according to another example of the present disclosure.

In an example, each of the detector units may transmit the acquired data to the reconstructing computer through the switch via the network bus. The method may specifically comprise the following steps.

In the step S501, a set of data acquired by a detector unit in a preset period may be compressed into a packet.

It should be appreciated that the preset period may be set according to actual requirements, for example, the preset period may be 50 us or 100 us. Each of the detector units in a preset period may acquire the data within a plurality of acquiring periods, such as three acquiring periods. Thus the compressing unit 311 in a preset period may compress a set of data acquired within three acquiring periods into a packet when the set of data is transmitted.

It should be noted that transmitting the packet to the reconstructing computer in the preset period may need each of the detector units to transmit the packet in the preset period to the reconstructing computer.

In the step S502, each of the detector units may sequentially transmit the packet itself to the reconstructing computer through the switch via the network bus according to an arrangement of the annular structure.

It should be noted that M*N detector units may sequentially transmit the packet either in series, or in parallel in rows or columns according to the arrangement of the annular structure.

For example, M*N packets within the first acquiring period may be firstly transmitted, then M*N packets within the second acquiring period may be transmitted, and so on.

The preset period may comprise n acquiring periods and n is an integer greater than 1. The data acquired by the detector unit may include data index, indicating whether the data is valid or not.

In the step S503, the reconstructing computer may decompress the packet transmitted by the detector unit into a set of decompressed data and separate the set of decompressed data according to the acquiring period.

In the step S504, a set of valid data may be obtained by eliminating invalid data in the set of separated data according to the acquiring period and the corresponding data index.

It should be noted that the data index may indicate the time corresponding to valid data. Because the time a γ photon generates is random, the data may not be acquired at all the acquiring periods. Thus, the data corresponding to a detector unit without acquiring any data (i.e., blank data) may be eliminated via the data index.

Hereafter, the reconstructing computer may perform a compliance process on the set of valid data and specifically include the following steps from S505 to S507.

In the step S505, the reconstructing computer may sort the set of valid data for each of the acquiring periods in a chronological order of the acquiring time information.

It should be noted that the sorting in an order of the preset time may take the acquiring period as a unit, i.e., the data for each of the acquiring periods are sorted in a chronological order of the acquiring time.

In the step S506, a set of first compliance data in a predetermined time length may be obtained by the reconstructing computer cutting the sorted set of data with a time window of the predetermined time length.

In the step S507, a set of second compliance data may be obtained by the reconstructing computer selecting a pair of compliance data within a predetermined position area from the set of first compliance data according to the location information and IP address. The set of second compliance data may be used to reconstruct an image.

The predetermined position area may refer to a range of a FOV. For example, a range of a FOV may be 270 degrees and a pair of data in the range of 270 degrees may be the second compliance data.

In a method provided in the disclosure, the reconstructing computer may receive all sets of original data transmitted by the detector, next all sets of data may be separated according to the acquiring period, and then invalid data (i.e. blank data) in the separated set of data may be eliminated according to the acquiring period and the corresponding data index. The set of valid data for each of the acquiring periods may be sorted in a chronological order of the acquiring time. A set of first compliance data may be obtained by cutting the sorted set of data with a time window of the predetermined time length. A set of second compliance data may be obtained by selecting a pair of compliance data within a predetermined position area from the set of first compliance data, where, the set of second compliance data may be used to reconstruct an image. Thus it can be seen that the compliance process performed on the sorted set of data may be directly performed by the reconstructing computer without the data discarded by other circuits and then performed the compliance process by the reconstructing computer. Thus, the reconstructing computer may efficiently obtain a pair of compliance data.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures may have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Specific implementations of functions and roles of modules in the above device may be seen in detail in implementations of corresponding blocks in above methods, which are not unnecessarily elaborated herein.

The above are only preferred examples of the present disclosure is not intended to limit the disclosure within the spirit and principles of the present disclosure, any changes made, equivalent replacement, or improvement in the protection of the present disclosure should contain within the range.

The methods, processes and units described herein may be implemented by hardware (including hardware logic circuitry), software or firmware or a combination thereof. The term 'processor', 'unit' and 'module' may be interpreted broadly to include a processing unit, ASIC, logic unit, a hardware component or programmable gate array etc in some embodiments. The processes, methods and functional units described herein may all be performed by the one or more processors; reference in this disclosure or the claims to a 'processor' should thus be interpreted to mean 'one or more processors'.

Further, the processes, methods and functional units described in this disclosure may be implemented in the form of a computer software product in some embodiments. The computer software product is stored in a storage medium and comprises a plurality of instructions for making a processor to implement the methods recited in the examples of the present disclosure.

The figures are only illustrations of an example, where the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A positron emission tomography (PET) imaging system, comprising:
a detector of an annular structure, including M*N detector units, both M and N being integers greater than 1, wherein
M detector units are evenly distributed on each circumferential direction of the annular structure,
N detector units are evenly distributed on each axial direction of the annular structure, and
each of the M*N detector units is allocated with an Internet Protocol (IP) address;
a rotational movement control module configured to control movement of a rod source of the PET imaging system, wherein the rod source is taken as a radiation emission calibrating source to emit γ photons to be detected by the detector;
a bed movement control module configured to control movement of a scanning bed of the PET imaging system;
a power control module configured to control power supply for the PET imaging system;
a reconstructing computer configured to
perform a coincidence detection process on all sets of data acquired by the detector according to location information, acquired time information and IP address, and
reconstruct an image with coincidence data determined by the coincidence detection process; and
a switch configured to connect with the detector, the rotational movement control module, the bed movement control module, the power control module and the reconstructing computer via a network bus, wherein
the switch, the detector, the rotational movement control module, the bed movement control module, the power control module and the reconstructing computer form a star-shaped network topology;
communication between the switch, the detector, the rotational movement control module, the bed movement control module, the power control module and the reconstructing computer is by way of the network bus; and
each of the M*N detector units are enabled to transmit data including the location information, acquired time information and IP address to the switch and the switch is enabled to forward received data to the reconstructing computer based on the network bus.

2. The system of claim 1, wherein each of the detector units comprises:
a compression unit configured to compress a set of data acquired by one of the M*N detector unit in a preset period into a packet;
a transmission unit is configured to sequentially transmit the packet output by the compression unit to the reconstructing computer through the switch via the network bus according to an arrangement of the annular structure.

3. The system of claim 2, wherein,
the preset period comprises n acquiring periods and n is an integer greater than 1;
the data acquired by the detector unit includes data index indicating whether the data is valid or not, wherein the data index is represented by acquired time information; when the data acquired by the detector unit includes the data index, the data is valid; and when the data acquired by the detector unit does not include the data index, the data is invalid.

4. The system of claim 3, wherein the reconstructing computer comprises:
a decompression unit configured to decompress the packet transmitted by the transmission unit into a set of decompressed data;
a separation unit configured to separate the set of decompressed data output by the decompressed unit according to the acquiring period; and
a culling unit configured to obtain a set of valid data by eliminating invalid data from the set of data separated by the separation unit according to the acquiring period and the corresponding data index.

5. The system of claim 4, wherein the reconstructing computer further comprises:
a sorting unit configured to sort the set of valid data for each of the acquiring periods in a chronological order of the acquiring time information;
a first coincidence data obtaining unit configured to obtain a set of first coincidence data in a predetermined time length by cutting the sorted set of data output by the sorting unit with a time window of the predetermined time length; and
a second coincidence data obtaining unit configured to obtain a set of second coincidence data by selecting a pair of coincidence data within a predetermined position area from the set of first coincidence data according to the location information and IP address, wherein, the set of second coincidence data is to be used to reconstruct an image.

6. The system of claim 1, wherein the number of N is pre-configured.

7. A method of a positron emission tomography (PET) imaging with a PET imaging system,
the system comprises:
a detector of an annular structure, including M*N detector units, both M and N being integers greater than 1, wherein
M detector units are evenly distributed on each circumferential direction of the annular structure,
N detector units are evenly distributed on each axial direction of the annular structure, and
each of the M*N detector units is allocated with an IP address;
a rotational movement control module configured to control movement of a rod source of the PET imaging system, wherein the rod source is taken as a radiation emission calibrating source to emit γ photons to be detected by the detector;
a bed movement control module configured to control movement of a scanning bed of the PET imaging system;
a power control module configured to control power supply of the PET imaging system;
a reconstructing computer; and
a switch configured to connect with the detector, the rotational movement control module, the bed movement control module, the power control module and the reconstructing computer via a network bus, wherein
the switch, the detector, the rotational movement control module, the bed movement control module, the power control module and the reconstructing computer form a star-shaped network topology;
communication between the switch, the detector, the rotational movement control module, the bed movement control module, the power control module and the reconstructing computer is by way of the network bus;

the method comprises:
- transmitting all sets of data acquired by the detector to the switch;
- forwarding received data to the reconstructing computer based on the network bus, wherein, the data includes location information, acquired time information and IP address;
- performing a coincidence detection process by the reconstructing computer on all sets of data acquired by the detector according to the location information, acquired time information and IP address; and
- reconstructing an image by the reconstructing computer with the coincidence detection data determined by the coincidence detection process.

8. The method according to claim 7, wherein said transmitting all sets of data acquired by the detector to the switch comprises:
- compressing a set of data acquired by a detector unit in a preset period into a packet;
- sequentially transmitting the packet by the detector unit to the switch.

9. The method according to claim 8, wherein,
- the preset period comprises n acquiring periods and n is an integer greater than 1;
- the data acquired by the detector unit includes data index indicating whether the data is valid or not, wherein the data index is represented by acquired time information;
- when the data acquired by the detector unit includes the data index, the data is valid; and when the data acquired by the detector unit does not include the data index, the data is invalid.

10. The method according to claim 9, wherein before performing a coincidence detection process by the reconstructing computer on all sets of data acquired by the detector, the method further comprises:
- decompressing the packet transmitted by the switch into a set of decompressed data;
- separating the set of decompressed data according to the acquiring period; and
- obtaining a set of valid data by eliminating invalid data from the set of separated data according to the acquiring period and the corresponding data index.

11. The method according to claim 10, wherein performing a coincidence process by the reconstructing computer on all sets of data acquired by the detector further comprises:
- sorting the set of valid data for each of the acquiring periods by the reconstructing computer in a chronological order of the acquired time information;
- obtaining a set of first coincidence data in a predetermined time length by the reconstructing computer cutting the sorted set of data with a time window of the predetermined time length; and
- obtaining a set of second coincidence data by the reconstructing computer selecting a pair of coincidence data within a predetermined position area from the set of first coincidence data according to the location information and IP address, wherein, the set of second coincidence data is used to reconstruct an image.

12. The method according to claim 7, wherein the number of N is pre-configured.

* * * * *